(12) United States Patent
Wong

(10) Patent No.: US 7,033,498 B2
(45) Date of Patent: Apr. 25, 2006

(54) CARTRIDGES USEFUL IN CLEANING DIALYSIS SOLUTIONS

(75) Inventor: Raymond J. Wong, Norman, OK (US)

(73) Assignee: Renal Solutions, Inc., West Lafayette, IN (US)

( * ) Notice: Subject to any disclaimer, the term of this patent is extended or adjusted under 35 U.S.C. 154(b) by 450 days.

(21) Appl. No.: 09/996,505

(22) Filed: Nov. 28, 2001

(65) Prior Publication Data

US 2002/0112609 A1    Aug. 22, 2002

Related U.S. Application Data

(63) Continuation-in-part of application No. 09/723,396, filed on Nov. 28, 2000, now Pat. No. 6,627,164.

(51) Int. Cl.
| C02F 1/00 | (2006.01) |
| C02F 1/44 | (2006.01) |
| C02F 1/42 | (2006.01) |
| B01D 15/00 | (2006.01) |
| B01D 39/00 | (2006.01) |

(52) U.S. Cl. ............... 210/321.71; 210/660; 210/663; 210/502.1; 210/503; 210/509; 210/807; 210/264; 210/284; 428/402

(58) Field of Classification Search ............ 210/321.71, 210/635, 656, 660, 661, 195.2, 198.2, 638, 210/502.1, 503, 509, 648, 663, 264, 284, 210/804; 428/402; 423/323, 419.1, 304, 423/308–311

See application file for complete search history.

(56) References Cited

U.S. PATENT DOCUMENTS

| 2,328,381 A | 8/1943 | Jaffe ........................ 285/161 |
| 3,520,298 A | 7/1970 | Lange ........................ 128/213 |
| 3,545,438 A | 12/1970 | De Vries .................... 128/213 |
| 3,669,878 A | 6/1972 | Marantz et al. ............... 210/22 |
| 3,669,880 A | 6/1972 | Marantz et al. ............... 210/22 |
| 3,685,680 A | 8/1972 | Tenckhoff et al. ............ 220/27 |
| 3,697,410 A | 10/1972 | Johnson et al. ............. 204/301 |
| 3,697,418 A | 10/1972 | Johnson ........................ 210/22 |
| 3,703,959 A | 11/1972 | Raymond .................... 210/87 |
| 3,850,835 A | 11/1974 | Marantz et al. ............. 252/182 |
| 3,888,250 A | 6/1975 | Hill ........................... 128/214 |
| 3,939,069 A | 2/1976 | Granger et al. ............... 210/22 |
| 3,989,622 A | 11/1976 | Marantz et al. .......... 210/22 R |
| 3,989,625 A | 11/1976 | Mason ........................ 210/94 |
| 4,025,608 A | 5/1977 | Tawil et al. ................ 423/305 |
| 4,042,672 A | 8/1977 | Brugger et al. ............. 423/419 |
| 4,088,456 A | 5/1978 | Giorgi et al. ................. 55/179 |
| 4,190,047 A | 2/1980 | Jacobsen et al. ............ 128/213 |
| 4,192,748 A | 3/1980 | Hyden ........................ 210/87 |

(Continued)

FOREIGN PATENT DOCUMENTS

EP    000152717 A1    8/1985    .................. 604/29

(Continued)

OTHER PUBLICATIONS

International Search Report for PCT/US01/44623.

(Continued)

Primary Examiner—W. L. Walker
Assistant Examiner—K S Menon
(74) Attorney, Agent, or Firm—Kilyk & Bowersox, P.L.L.C.

(57) ABSTRACT

Cartridges useful in regenerating or purifying dialysis solutions are described as well as methods to regenerate or purify spent dialysis solutions. Dialysis systems using the sorbent cartridges of the present invention are further described.

57 Claims, 7 Drawing Sheets

U.S. PATENT DOCUMENTS

| | | | |
|---|---|---|---|
| 4,213,859 A | 7/1980 | Smakman et al. ............. 210/27 |
| 4,256,718 A | 3/1981 | McArthur et al. ....... 423/419 P |
| 4,360,507 A | 11/1982 | McArthur et al. ....... 423/419 P |
| 4,412,917 A | 11/1983 | Ahjopalo .................... 210/104 |
| 4,460,555 A | 7/1984 | Thompson .................. 423/309 |
| 4,473,449 A | 9/1984 | Michaels et al. ........... 204/101 |
| 4,474,853 A | 10/1984 | Watanabe .................... 428/403 |
| 4,484,599 A | 11/1984 | Hanover et al. ......... 137/636.1 |
| 4,495,129 A | 1/1985 | Newberry et al. .......... 264/235 |
| 4,521,528 A | 6/1985 | Kovach ....................... 502/208 |
| 4,542,015 A * | 9/1985 | Smakman et al. .......... 424/462 |
| 4,558,996 A | 12/1985 | Becker ........................ 417/374 |
| 4,560,472 A | 12/1985 | Granzow et al. ........... 210/140 |
| D282,578 S | 2/1986 | Humphreys et al. ......... D24/21 |
| 4,650,587 A | 3/1987 | Polak et al. ................ 210/638 |
| 4,680,122 A | 7/1987 | Barone ....................... 210/637 |
| 4,738,668 A | 4/1988 | Bellotti et al. .............. 604/283 |
| 4,765,907 A | 8/1988 | Scott .......................... 210/648 |
| 5,004,459 A | 4/1991 | Peabody et al. .............. 604/29 |
| 5,032,261 A | 7/1991 | Pyper ......................... 210/137 |
| 5,034,124 A | 7/1991 | Kopf ........................... 210/231 |
| 5,035,805 A | 7/1991 | Freeman et al. ............ 210/689 |
| 5,151,082 A | 9/1992 | Gorsuch et al. ............... 604/4 |
| 5,173,125 A | 12/1992 | Felding .................... 134/22.11 |
| 5,234,603 A * | 8/1993 | Potts .......................... 210/719 |
| 5,427,683 A | 6/1995 | Gershon et al. ............ 210/264 |
| 5,498,338 A | 3/1996 | Kruger et al. ............... 210/641 |
| 5,520,632 A | 5/1996 | Leveen et al. ................. 604/9 |
| 5,549,674 A | 8/1996 | Humes et al. ................ 623/11 |
| 5,595,909 A | 1/1997 | Hu et al. .................. 435/297.4 |
| 5,597,805 A | 1/1997 | Breborowicz et al. ........ 514/19 |
| 5,631,025 A | 5/1997 | Shockley et al. ........... 424/678 |
| 5,641,405 A | 6/1997 | Keshaviah ................... 210/645 |
| 5,679,231 A | 10/1997 | Alexander et al. .......... 204/627 |
| 5,704,915 A | 1/1998 | Melsky et al. .............. 604/175 |
| 5,712,154 A | 1/1998 | Mullon et al. ........... 435/297.4 |
| 5,782,796 A | 7/1998 | Din et al. ...................... 604/29 |
| 5,824,213 A | 10/1998 | Utterberg ..................... 210/241 |
| 5,938,634 A | 8/1999 | Packard ........................ 604/29 |
| 5,944,684 A | 8/1999 | Roberts et al. ................. 604/5 |
| 5,955,450 A | 9/1999 | Breborowicz et al. ........ 514/54 |
| 5,968,966 A | 10/1999 | Bergström .................. 514/400 |
| 5,980,481 A | 11/1999 | Gorsuch ....................... 604/28 |
| 5,984,891 A | 11/1999 | Keilman et al. |
| 6,017,942 A | 1/2000 | Bergström .................. 514/399 |
| 6,074,359 A | 6/2000 | Keshaviah et al. ........... 604/29 |
| 6,117,122 A | 9/2000 | Din et al. .................... 604/408 |
| 6,146,536 A | 11/2000 | Twardowski ................ 210/646 |
| 6,196,992 B1 | 3/2001 | Keilman et al. .............. 604/67 |
| 6,274,103 B1 | 8/2001 | Taylor ........................ 422/261 |
| 6,284,131 B1 | 9/2001 | Hogard et al. .............. 210/143 |
| 6,284,139 B1 | 9/2001 | Piccirillo .................... 210/645 |
| 6,293,921 B1 | 9/2001 | Shinmoto et al. ............. 604/29 |
| 6,299,769 B1 | 10/2001 | Falkvall et al. ............. 210/232 |
| 6,306,836 B1 | 10/2001 | Martis et al. ................. 514/58 |
| 6,309,673 B1 | 10/2001 | Duponchelle et al. ...... 424/717 |
| 2003/0105424 A1 | 6/2003 | Karoor et al. ................ 604/29 |

FOREIGN PATENT DOCUMENTS

| | | |
|---|---|---|
| FR | 2 585 251 A1 | 5/1985 |
| FR | 2585251 | 1/1987 |
| GB | 1 467 880 | 3/1977 |
| JP | 59 046964 | 3/1984 |
| JP | 3-242206 | 10/1991 |
| JP | 08187284 | 7/1996 |
| SU | 1770285 A1 | 10/1992 |

OTHER PUBLICATIONS

International Search Report for PCT/US01/44660.
U.S. Appl. No. 09/995,888.
U.S. Appl. No. 09/723,396.
Cobe Renal Care, Inc., "Guide to Custom Dialysis," Product No. 306100-005; Revision E, 9/93, pp. 1-54.
Cobe Renal Care, Inc., "Sorbent Dialysis Primer," Product No. 306100-006; Edition 4, 9/93, pp. 1-51.
"Augmentation of Efficiency by Continuous Flow Sorbent Regeneration Peritoneal Dialysis", A. Gorden et al.. vol. XXII Trans. Amer. Soc. Artif. Int. Organs, 1976, pp. 599-604.
"Centrifugal Artifical Kidney", R. M. Kellogg, IBM Technical Disclosure Bulletin, vol. 14, No. 11, Apr. 1972, pp. 3433-3435.
"Combined Technological-Clinical Approach To Wearable Dialysis", Robert L. Stephen et al., Kidney International, vol. 13, Suppl. 8 (1978), pp. S-125-S-132.
"Development of Continuous Recirculating Peritoneal Dialysis Using a Double Lumen Catheter", Michio Mineshima et al., ASAIO Journal, 1992, pp. M377-M381.
"Important Devices in Biomedical Engineering", John G. Webster, International Biomedical Engineering Days, 1992, pp. 1-9.
"Recirculation Peritoneal Dialysis with Sorbent Redy Cartridge", Rasib M. Raja et al., Nephron 16, (1976), pp. 134-142.
"Recirculating Peritoneal Dialysis with Subcutaneous Catheter", R. L. Stephen et al., American Society For Artificial Internal Organs, vol. XXII, 1976, pp. 575-584.
"Sorbent Based Regenerating Delivery System For Use In Peritoneal Dialysis", A. J. Lewin et al., vol. XX Trans. Amer. Soc. Artif. Int. Organs, 1974, pp. 130-134.
"The Use of Reciprocating Peritoneal Dialysis with a Subcuntaneous Peritoneal Catheter in End-Stage Renal Failure in Diabetes Mellitus", G. D. Warden et al., Journal of Surgical Research, vol. 24, Jun. 1978, pp. 495-500.
"Blood Flow and Pressure Measurement", IBM Technical Disclosure Bulletin, Feb. 1971.
"Continous Flow Dialyzer", IBM Technical Disclosure Bulletin, Jul. 1975.
"Reciprocating Peritoneal Dialysis", Carl Kablitz, M.D. et al., Dialysis & Transplantation, vol. 7, No. 3, Mar. 1978, pp. 211-212 and 214.
"Reciprocating Peritoneal Dialysis with a Subcuntaneous Peritoneal Catheter", Robert L. Stephen, M.D., Dialysis & Transplantation, vol. 7, No. 8, Aug. 1978.
"Studies on low-cost Disposable Bioreactor for Bilirubin Detoxification", B. Das et al., Proceedings RC IEEE-EMBS & 14th BMESI, 1995, 4.53-4.54.
"Technological Augmentation of Peritoneal Urea Clearance: Past, Present, and Future", Carl Kablitz, M.D. et al., Dialysis & Transplantation, vol. 8, No. 8, Aug. 1960, pp. 741-744 and 778.
E-mail-(1995) D. Halligan, "The Human and Artificial Kidney" from Google Search.
"A Membrane System to Remove Urea from the Dialyzing Fluid of the Artificial Kidney" Kolff, W. J. et al., Annual rept. No. 2, Jul. 1, 1978-Jun. 30, 1979).
"The Regenerative Dialysis (REDY) Sorbent System" Roberts M., Nephrology, 1998, V4, N4 (Aug), P275-278.
"In search of a 24 Hours Per Day Artificial Kidney" Lande A. J. et al., Journal of dialysis (U.S.) 1977, 1 (8) p. 805-23, ISSN 0362-8558.
Efficacy of Lumbo-Peritoneal Versus Ventriculo-Peritoneal Shunting for Management of Chronic.

Hydrocephalus Following Aneurysmal Subarachnoid Haemorrhage Kang S., Acta Neurochirurgica. 142 (1):p. 45-49 2000.

"Performance of the Dialytic Reactor with Product Inhibited Enzyme Reactions: A Model Study" Catapano Gerardo et al., Bioseparation 4 (3):p. 201-211 1994.

"Carbonato-Compounds of Zirconium" Russian Journal of Inorganic Chemistry, vol. 11, No. 8, Aug. 1996, pp. 995-1004.

* cited by examiner

Figure 7  Fluid Regeneration Test System

CARTRIDGES USEFUL IN CLEANING DIALYSIS SOLUTIONS

This is a continuation-in-part application of U.S. patent application Ser. No. 09/723,396 filed Nov. 28, 2000, now U.S. Pat. No. 6,627,164 which is incorporated in its entirety by reference herein.

BACKGROUND OF THE INVENTION

The present invention relates to cartridges such as ion exchange cartridges or adsorption cartridges which are useful, for instance, in dialysis. In particular, the present invention relates in general to the regeneration or purification of used dialysate fluids. The present invention further relates to methods of conducting dialysis using certain cartridges and also relates to methods of making the cartridges.

Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. If medical treatment is sought at that time, progression can be slowed. Late stage chronic renal failure is when kidney function has decreased to 15%. End stage renal failure is when kidney function is at 5% of normal. Death will most likely result without treatment at this point. As of 1998, there were 430,000 patients in the United States diagnosed with chronic renal failure, wherein the average life expectancy of a chronic renal failure patient is 2½ years. Some do live 20 years or more. Also, there are approximately as many patients yearly with acute renal failure as with chronic renal failure, approximately ½ of these patients need treatment. On the whole, acute patients are sicker and less stable than chronic patients. They are frequently in ICU or CCU and can't be moved. Acute patients die, recover kidney function, or go on to become chronic dialysis patients. There is no current cure for renal disease. However, one treatment is transplantation, which is where a human kidney is surgically placed in the body and connected to the bladder. Daily medication is needed to keep the body from rejecting the transplanted kidney. Also, there is peritoneal dialysis (PD). With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Also, there is hemodialysis. This is a method of blood purification in which blood is continually removed from the body and passed through a dialyzer (artificial kidney) where metabolic waste and excess water are removed and pH and acid/base balance are normalized. The blood is simultaneously returned to the body. The dialyzer is a small disposable device consisting of a semi-permeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit which acts to pump and control pressures, temperatures, and electrolyte concentrations of the blood and the dialysate. The average length of one hemodialysis treatment is 3–5 hours.

There are several types of hemodialysis:

a) Single Pass—hemodialysis is the most common treatment for renal disease. Most hemodialysis treatments are performed with single pass dialysis machines. They are called single pass because the dialysate (cleaning solution) passes by the blood in the dialyzer one time and then is disposed. Single pass dialysis machines generally require:

1) a water source capable of delivering at least 1000–1500 ml/min (assuming a 50% rejection rate by the R.O. system)

2) a water purification system sufficient of providing a continuous flow of 500–800 ml/min of purified water.

3) an electrical circuit of at least 15 amps in order to pump and heal 500–800 ml of water/min.

4) a floor drain or any other receptacle capable of accommodating at least 500 ml of used dialysate/minute as well as the rejected water from the R.O. system.

b) Sorbent Dialysis 1) does not require a continuous water source, a separate water purification machine or a floor drain because it continuously regenerates a small volume of dialysate and incorporates a water treatment system within the machine. Therefore, sorbent systems are truly portable.

2) sorbent systems require only a 5 amp electrical source because they recycle the same small volume of dialysate throughout the dialysis procedure. The heavy duty dialysate pumps and heaters used for large volumes of dialysate in single pass dialysis are not needed.

3) the sorbent system can use 6 liters of tap water from which dialysate is made for an entire treatment.

4) the sorbent system uses a sorbent cartridge—which acts both as a water purifier and as a means to regenerate used dialysate into fresh dialysate. The infusate system acts with it to properly balance the electrolyte composition of the regenerated dialysate.

The sorbent cartridge containing zirconium phosphate (ZrP) and hydrous zirconium oxide (HZO) ion-exchange materials has been historically used for the REDY regeneration hemodialysis system. The scheme of the REDY cartridge is shown in FIG. 1.

The principle of the REDY cartridge is based on the hydrolysis of urea to ammonium carbonate by the enzymatic reaction of urease. The ammonia and ammonium ions are then removed by the zirconium phosphate (NaHZrP) in exchange for the hydrogen ions and $Na^+$ ions, which are counter-ions in the cation exchanger. ZrP also serves as cation exchanger to remove Ca, Mg, K, and all toxic metals in dialysate, thus allowing to maintain a balance of electrolyte level in the patient's blood (Ca, Mg, K) by using an infusate system, as well as providing safety for dialysis treatment with regard to water quality. The carbonate from the urea hydrolysis then combines with the hydrogen ions in NaHZrP to form bicarbonate, which is delivered to the uremic patient as a base to correct for acidosis. The hydrous zirconium oxide (HZO) containing acetate as a counter ion serves as an anion exchanger to remove phosphate from uremic patients for the treatment of hyperphosphatemia. The material also prevents leaching of phosphate from NaHZrP and removes toxic anions (e.g., fluoride) in water that may cause harm to a patient during dialysis. The acetate released during ion exchange is also a base to correct for acidosis by acetate metabolism. The granular activated carbon in the cartridge is responsible for the removal of creatinine, uric acid, and nitrogenous metabolic waste of the patient as well as chlorine and chloramine from water. Thus the REDY regenerative dialysis system is efficient to provide both safety and simplicity of water treatment and hence convenience for hemodialysis. The efficacy and safety record of the system has been well established. Nevertheless, the REDY cartridge can produce a variation of dialysate composition and pH during the treatment with a continuous release of $Na^+$ by the cartridge. Thus the REDY dialysis therapy has to provide several dialysate prescriptions to balance the $Na^+$ level in the patient for the correction of hyper and hyponatremia. Also a conductivity alarm system is generally present to keep the $Na^+$ level in the dialysate below a safe limit with proper dilution. The $Na^+$ and bicarbonate level in the dialysate may vary with the BUN level of the patient.

In the area of peritoneal dialysis (PD), particular emphasis has to be put on (1) a minimum variation of dialysate composition and pH during the PD treatment and (2) cost and size of the cartridge. For example, the adsorption capacity requirement of sorbent PD may be lower than that of REDY cartridge. The variation of dialysate composition is particularly important since PD is a slow treatment with treatment duration up to 2–4 hours per day. Excessive donation of $Na^+$ by the cartridge to the patient should be avoided during the treatment. In order to control the release of $Na^+$, an understanding of the ion exchange mechanism of ZrP with ammonium ions and dialysate cations (Ca, Mg, K, and Na) is needed.

ZrP is an inorganic cation exchange material with the molecular structure as shown below:

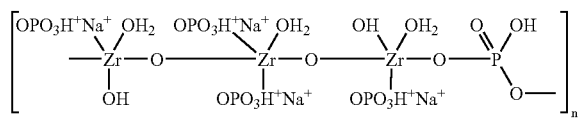

It contains both $H^+$ and $Na^+$ as counter-ions, which are responsible for ion exchange. The relative content of these ions in ZrP can be controlled by the pH to which acid ZrP (or $H^+ZrP$) is titrated with NaOH. The composition of the resultant product of titration, $Na_x^+H_{2-x}^+ZrP$, may vary during the following ion exchange processes in dialysate:

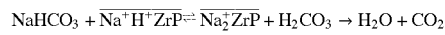

The relative release of $Na^+$ and $H^+$ by ZrP during the ion exchange depends on the ion exchange equilibrium of these ions in ZrP with other cations in the liquid phase. The equilibrium may shift as the composition of $Na^+H^+ZrP$ and liquid phase continue to change during the ion exchange process.

Based on the ion exchange principle, the $Na^+$ release from ZrP can be controlled by shifting to the conditions that favor the dominant release of $H^+$ ions. This concept can be important for the design of sorbent cartridge formulations for the PD fluid regeneration.

The current method of making ZrP for the REDY cartridge is titrating acid ZrP ($H^+ZrP$) to the pH range 6.25–6.45 in a NaCl/NaAc buffer to produce $Na^+H^+ZrP$ with high $Na^+$ content. This will trigger the $Na^+$ release especially in acetate or lactate dialysate with low buffer capacity and at low pH. Thus the ZrP quality made for the REDY cartridge may not be suitable for the PD fluid regeneration application. In order to remove this limitation, as shown in the present invention, a modification is made by using $Na^+H^+ZrP$ with lower specified $Na^+$ content. This material can be made by titrating the acid ZrP ($H^+ZrP$) to a lower pH range 5.5–6.0 in deionized water. Another limitation of the REDY cartridge for PD treatment is that the hydrous zirconium oxide loaded with acetate is an acidic material. Thus the low pH of dialysate resulted from the acidity of this material will trigger a release of $Na^+$ and an initial loss of bicarbonate due to the reaction.

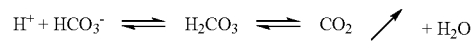

If the current REDY cartridge is used for PD treatment, it may produce a continuous rise of $Na^+$ concentration up to 170 mEq/l due to dominant $Na^+$ exchange throughout the treatment. In addition, an initial dip of $Na^+$. $HCO_3$ and pH may occur due to short time $H^+$ exchange.

Accordingly, in the area of dialysis, especially with respect to PD treatment, it would be beneficial to overcome one or more of the above-described disadvantages.

SUMMARY OF THE PRESENT INVENTION

A feature of the present invention is to provide materials which are useful in the regeneration or purification of solutions containing waste products.

A further feature of the present invention is to provide materials which are useful in the regeneration or purification of dialysis solutions such as peritoneal dialysis solutions or other dialysate solutions such as those used in hemodialysis.

A further feature of the present invention is to provide a system wherein dialysis solutions can be regenerated in order to avoid large quantities of dialysis solution and to avoid the discarding of spent dialysis solutions.

An additional feature of the present invention is to overcome one or more of the above-described difficulties.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, as embodied and broadly described herein, the present invention relates to a sorbent cartridge that contains at least sodium zirconium carbonate. In a preferred embodiment, the sodium zirconium carbonate is present as at least one layer in a sorbent cartridge. In another preferred embodiment, zirconium phosphate is additionally present.

The present invention further relates to a sorbent cartridge that contains at least sodium-Group IV B metal carbonate or other alkali metal-Group IV B metal carbonate. The alkali metal-Group IV B metal carbonate is preferably present as a layer in the sorbent cartridge. Furthermore, a Group IV B metal phosphate can additionally be present in the sorbent cartridge.

The present invention also relates to a method of making the sorbent cartridge comprising introducing sodium zirconium carbonate into a cartridge.

The present invention further relates to the formation of sorbent cartridges by the introduction of an alkali metal-Group IV B metal carbonate into a cartridge.

In addition, the present invention relates to a method to regenerate spent dialysis solutions, which can for instance be peritoneal dialysis solutions or hemodialysis solutions. The method can involve passing spent dialysis solution through a cartridge that contains at least sodium zirconium carbonate or an alkali metal-Group IV B metal carbonate and/or other materials described herein, in order to regenerate the dialysis solutions so that the dialysis solutions can be used again to purify and remove waste products from blood, for instance, through peritoneal dialysis or hemodialysis (e.g., sorbent dialysis).

The present invention also relates to a sorbent dialysis system comprising a sorbent cartridge, wherein the sorbent cartridge contains at least sodium zirconium carbonate or an alkali metal-Group IV B metal carbonate. The system can be a single pass dialysis system or a sorbent dialysis system. This system with respect to a sorbent dialysis system further preferably contains an infusate pump, a dialyzer, a pump, and a reservoir all interconnected in an operating system as shown for instance in FIG. 2.

It is to be understood that both the foregoing general description and the following detailed description are exemplary and explanatory only and are intended to provide a further explanation of the present invention, as claimed.

The accompanying drawings, which are incorporated in and constitute a part of this application, illustrate several embodiments of the present invention and together with the description, serve to explain the principles of the present invention.

DETAILED DESCRIPTION OF THE PRESENT INVENTION

Figure 1:
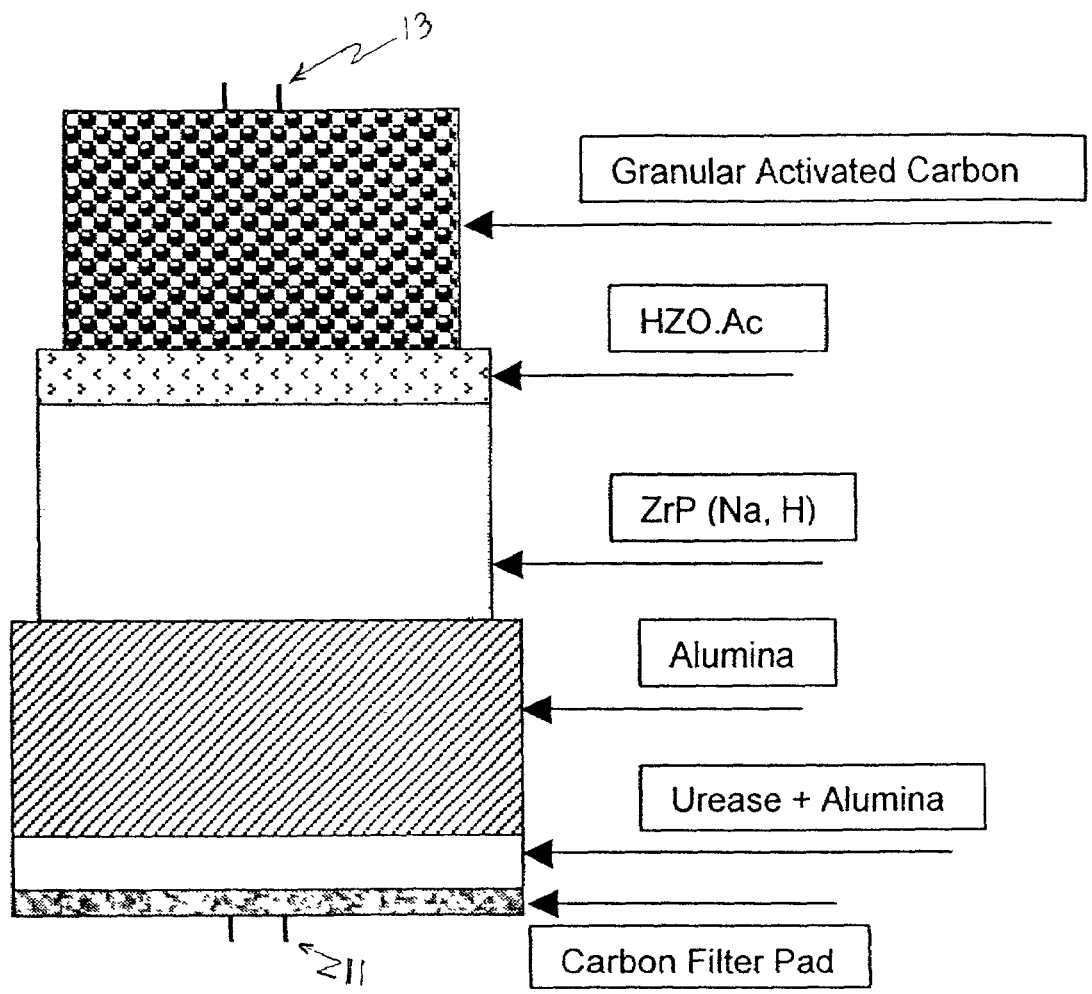
FIG. 1 is a schematic diagram showing a REDY® cartridge.

The present invention relates to materials useful for separation processes such as the removal of waste products and excess fluid that accumulates in dialysate fluids. These materials are preferably present in a container (i.e., a cartridge) capable of holding the materials useful for the separation process. In a preferred embodiment, the materials described in detail below or the arrangement of various materials are preferably used in a dialysis system or other similar type of system that is useful for the removal of waste products and/or excess fluid that accumulates in dialysate fluids, for instance, as a result of conducting dialysis. As described in more detail below, the present invention is useful in purifying or regenerating dialysate fluids used in peritoneal dialysis (PD) and in hemodialysis (HD). For purposes of the present invention, a dialysis solution means a peritoneal dialysis solution or dialysate fluids that are useful in hemodialysis or sorbent dialysis systems. Conventional dialysis solutions for PD or HD can be used and regenerated by the present invention and are known to those skilled in the art.

In one embodiment of the present invention, the present invention relates to a sorbent cartridge that contains at least an alkali metal-Group IV B metal carbonate. (Group IV B is with reference to a column in the Periodic Table.) Examples of the Group IV B metal are titanium, zirconium, and hafnium. Preferably, the Group IV B metal is zirconium and therefore the preferred material in the sorbent cartridge is sodium zirconium carbonate. Any type of alkali metal-Group IV B metal carbonate can be used as long as the alkali metal-Group IV B metal carbonate is preferably capable of acting as a phosphate adsorbent. Preferably, the alkali metal present is sodium. The sodium-Group IV B metal carbonate preferably acts as a bicarbonate provider or donor and therefore other materials capable of acting as a bicarbonate provider or donor can be also be used or alternatively can be used in the present invention. Other pH buffer materials that can be used as a bicarbonate provider in this invention include encapsulated sodium bicarbonate and ion exchange resins in carbonate form, and the like.

As indicated above, the sodium-Group IV B metal carbonate is preferably a sodium zirconium carbonate. In lieu of the sodium-Group IV B metal carbonate, an alkali metal other than sodium can be used, such as potassium and the like (e.g., potassium-Group IV B metal carbonate, such as potassium zirconium carbonate). More preferably, the sodium zirconium carbonate has one or more of the following characteristics.

The alkali metal-Group IV B metal carbonate, e.g., sodium zirconium carbonate, preferably has an average particle size of from about 30 microns to about 50 microns, and other particle size ranges can be used.

The sodium zirconium carbonate of the present invention preferably, in its final form, has from about 2 wt % to about 5 wt % $Na^+$;

from about 44 wt % to about 50 wt % $ZrO_2$;

from about 12 wt % to about 18 wt % $CO_3^{2-}$; and from about 30 wt % to about 40 wt % LOD, based on the weight of the sodium zirconium carbonate, wherein LOD is the amount of weight lost on drying of the SZC. The majority of the LOD will be $H_2O$.

The sodium zirconium carbonate of the present invention preferably satisfies the standards set forth in ANSI/AAMI RD-5-1992 on extractable toxic impurities.

Preferably, the sodium zirconium carbonate of the present invention achieves one or more of the following properties or characteristics:

a phosphate adsorption having a minimum capacity of from about 30 to about 35 mg $PO_4$-P/gm SZC; other capacities can be used;

a minimum $HCO_3^-$ content of from about 2 to about 4 mEq $HCO_3^-$/gm SZC; other amounts can be present;

a maximum leachable $Na^+$ content of from about 1.5 to about 2.0 mEq $Na^+$/gm SZC; other amounts can be present;

and/or a pH range of the titrated sodium zirconium carbonate of from about 6 to about 7. Other pHs can be used.

Preferably, the sodium zirconium carbonate of the present invention has at least one of the above characteristics and more preferably at least two or three, and even more preferably, all of the above characteristics.

The sodium zirconium carbonate preferably provides the necessary potency requirements for peritoneal dialysis or hemodialysis applications by providing a sufficient phosphate adsorption capacity for economic use as a clinical sorbent for the treatment of, for instance, hyperphosphatemia of renal disease patients. Further, the sodium zirconium carbonate of the present invention preferably provides the specified bicarbonate content in a peritoneal dialysis or hemodialysis fluid during applications. The present invention further has the minimum leachable $Na^+$ as described above.

More details of various materials and methods of making the materials are described, for instance, in U.S. patent application Ser. No. 09/723,396 filed Nov. 28, 2000, which is incorporated in its entirety by reference herein and forms a part of the present application.

While any amount of the alkali metal-Group IV B metal carbonate can be used in the sorbent cartridge, preferably amounts effective to remove substantially all if not all of the phosphate in the waste material of the blood is present. For instance, amounts ranging from about 50 grams to about 250 grams of the sodium-Group IV B metal carbonate is present based on from about 20 to about 140 $mEqHCO_3^-/L$ dialysate. More preferably, the amount of the alkali metal-Group IV B metal carbonate is from about 80 to about 120 grams. Other amounts above and below the above-recited ranges can be used. For purposes of the present invention, all amounts provided throughout as preferred amounts are based on 20 to 140 $mEqHCO_3^-/L$ dialysate which is commonly used to determine the effectiveness of separation materials in the dialysis area. The examples of the present application further describe this simulated efficiency test.

Another component that can be optionally present in the sorbent cartridges of the present invention is an ammonia adsorbent such as a zirconium phosphate, zeolite, titanium phosphate, zirconium silicate, organic ionic exchange resins, and the like. Preferably, the ammonia adsorbent, if used, is a zirconium phosphate (ZrP), and is preferably titrated zirconium phosphate. Preferably the zirconium phosphate is titrated ZrP in the $Na^+$ and/or $H^+$ form. Preferably a mixture of $Na^+$ and $H^+$ are present in the ZrP.

More preferably, the zirconium phosphate has one or more of the following characteristics:

$H^+$ content of from about 1.4 to about 2.0 wt %;
$Na^+$ content of from about 4 to about 6 wt %;
$ZrO_2$ content of from about 34 to about 37 wt %;
$PO_4^-$ content of from about 41 to about 43 wt %; and
$H_2O$ content from about 14 to about 18 wt %, based on the weight of the zirconium phosphate. Other content amounts for the various characteristics can be used.

Furthermore, the zirconium phosphate of the present invention preferably has an adsorption capacity for ammonia, $Ca^{2+}$, $Mg^{2+}$, $K^+$, and toxic heavy metals. More preferably, the adsorption capacity is approximately from about 20 mg $NH_4$-N/gm ZrP to about 45 mg or more $NH_4$-N/gm ZrP, and more preferably at least about 30 mg $NH_4$-N/gm ZrP; from about 2 mEq $Ca^{2+}$/gm ZrP to about 7 mEq $Ca^{2+}$/gm ZrP, and more preferably at least about 3 mEq $Ca^{2+}$/gm ZrP; from about 1 mEq $Mg^{2+}$/gm ZrP to about 5 mEq $Mg^{2+}$/gm ZrP, and more preferably at least about 2 mEq $Mg^{2+}$/gm ZrP; and from about 3 mEq HM/gm ZrP to about 9 mEq HM/gm ZrP, and more preferably at least about 6 mEq HM/gm ZrP for heavy metals (HM).

Further, the zirconium phosphate preferably has a $Na^+$ content of from about 1.8 mEq $Na^+$/gm ZrP to about 3 mEq $Na^+$/gm ZrP, and more preferably about 2.4 mEq $Na^+$/gm and a pH of from about 5.5 to about 6. Other pHs can be used and different $Na^+$ contents can be used.

Also, the zirconium phosphate of the present invention preferably has a minimum leachable $PO_4^{3-}$ for the material and more preferably is less than about 0.05 mg $PO_4^{3-}$/gm ZrP. Other amounts can be used.

In addition, the zirconium phosphate preferably has an average grain size of from about 30 to about 40 microns and has no residual sulfate or chloride (e.g., less than 0.01%). Other particle sizes can be used. Furthermore, the zirconium phosphate preferably satisfies the ANSI/AAMI RD-5-1992 standard on extractable toxic impurities and has a pH when in water of from about 6 to about 7.

Further details of the preferred zirconium phosphate and methods of making them, for instance, are described in U.S. patent application Ser. No. 09/723,396, as mentioned above.

The ammonia adsorbent, preferably zirconium phosphate, can be used in any amount. Preferably, the amount of the ammonia adsorbent is a sufficient amount to remove at least partially if not substantially or entirely all of the ammonia present in the spent fluids. More preferably, the amount of the ammonia adsorbent, and preferably zirconium phosphate, in a cartridge is from about 300 grams to about 750 grams and more preferably from about 500 to about 600 grams based generally on the dialysate mentioned above. This range is especially preferred for PD regeneration. Another range is preferably from about 800 grams to about 1900 grams in the cartridge and more preferably from about 1300 grams to about 1700 grams. These ranges are especially preferred by HD regeneration. Thus, overall ranges for the cartridge in general are from about 300 grams or less to about 1900 grams or more. Other amounts can be used.

Another component which can be present in the cartridges of the present invention is zirconium oxide and preferably hydrous zirconium oxide and more preferably hydrous zirconium oxide (HZO) containing acetate (HZO.Ac). The hydrous zirconium oxide containing acetate preferably acts as a counter ion and serves as an ion exchanger to remove phosphate from uremic patients. The hydrous zirconium oxide can also prevent leaching of phosphate from NaHZrP and removes toxic anions present in water that may cause harm to a patient during dialysis. The acetate released during ion exchange can also act as a base to correct for acidosis by acetate metabolism. The hydrous zirconium oxide described in the patents and publications below can be used herein. While the zirconium oxide and preferably hydrous zirconium oxide can be located anywhere in the cartridge, preferably in one embodiment, the hydrous zirconium oxide is adjacent or closer to the alkali metal-Group IV metal carbonate. Even more preferably, and especially for HD regeneration systems, hydrous zirconium oxide is blended with the alkali metal-Group IV metal carbonate (e.g., sodium zirconium carbonate). While any amount can be blended with the alkali metal-Group IV metal carbonate, preferably a weight ratio at or near a 1 to 1 weight ratio is used. Thus, from about 50 grams to about 300 grams are preferred. A preferred weight ratio of hydrous zirconium oxide containing acetate and the sodium zirconium carbonate is an amount of from 50 grams/50 grams to about 200 grams/200 grams and more preferably 100 grams/100 grams wherein the ratio signifies HZO-Ac to SZC. Other amounts can be used as well.

In addition, another component that can be present in the cartridges of the present invention is zirconium basic carbonate (ZBC) and/or other Group IV metal basic carbonates. Commercially available forms can be used as well as those described in any one of the patents and publications set forth below. A preferred Group IV metal carbonate is zirconium basic carbonate and more preferably has the following parameters:

a zirconium basic carbonate having $Na^+$ content of less than about 1000 ppm;

a $ZrO_2$ wt % of from about 35% to about 40%; and a $CO_3^{2-}$ wt % of from about 8% to about 10%, based on the weight of the zirconium basic carbonate. Other amounts for each of these parameters can be used.

Preferably, the zirconium basic carbonate has essentially no $SO_4^{2-}$ and essentially no $Cl^-$ in the zirconium basic carbonate, e.g., less than about 0.01 wt %. The ZBC can be used in any amount and preferably from about 100 grams to about 600 grams in a cartridge.

Further details of this material as well as preferred methods of making it can be found in U.S. patent application Ser. No. 09/723,396, as mentioned above and incorporated in its entirety by reference herein.

Other materials that can also be present in the sorbent cartridge include, but are not limited to, alumina, alumina supported urease, granulated activated carbon, activated alumina, zeolites, diatomaceous earth, direct urea sorbents, and other conventional adsorbent(s), fillers, glass beads, and the like. The materials, amounts, and other optional components and/or dialysis systems described in the following patents and publications can also be used in the present application and are incorporated in their entirety by reference herein and form a part of the present application: Des. 282,578, 3,669,878, 3,669,880, 3,697,410, 3,697,418, 3,703,959, 3,850,835, 3,989,622, 3,989,625, 4,025,608, 4,213,859, 4,256,718, 4,360,507, 4,460,555, 4,484,599, 4,495,129, 4,558,996; and the following articles, "Guide to Custom Dialysis," Product No. 306100-005, Revision E, pages 1–54, dated September 1993 and "Sorbent Dialysis Primer," Product No. 306100-006, Edition 4, pp. 1–51, dated September 1993 of Cobe Renal Care, Inc.

With respect to the sorbent cartridge, any combination of the above-described materials can be used. As indicated above, preferably the sorbent cartridge contains at least an alkali metal-Group IV B metal carbonate such as sodium zirconium carbonate.

The various combination of materials can be present as a mixture or present in any other type of arrangement. For instance, a series of cartridges can be used wherein the combination of the above-described materials can be present in one or more cartridges. For instance, the sodium zirconium carbonate can be present in one cartridge and the zirconium phosphate, for instance, can be present in a second cartridge, and optionally, the alumina is present in a third cartridge and so on. Alternatively, or in combination, one or more adsorbent cartridges can contain one or more of the above-described materials in any combination. Thus, for instance, sodium zirconium carbonate, for instance, can be present in one or more cartridges and the zirconium phosphate, for instance, can be present in the same or different cartridges and so on. More preferably, all of the materials are in a single cartridge and even more preferably arranged as layers in the cartridge.

Any effective amounts of the above-described materials can be optionally present in the cartridges of the present invention. For instance, alumina can be present in an amount of from about 100 grams or below to about 500 grams or above and more preferably from about 200 grams to about 350 grams and more preferably about 300 grams. A preferred particle size for the alumina is from about 20 microns or less to about 40 microns or more. The alumina is commercially available from sources like Alcoa. With respect to the immobilized urease, preferably the immobilized urease is present in an amount of from about 100 grams to about 300 grams and more preferably from about 200 grams to about 250 grams. Preferably the enzyme (e.g., urease) is immobilized by being mixed with a filler or the like such as alumina. A preferred source of urease is Jack Bean Meal commercially available from such sources as Sigma, preferably in the amount of from about 8 or less to 20 grams or more. Generally, the urease is present in an amount of from about 22,000 IU or less to about 55,000 IU or more, and more preferably from about 28,000 IU to about 42,000 IU. The particle size of the Jack Bean Meal can be any effective size such as about 40 mesh or less (or less than about 0.4 mm). The activated carbon may be present in any amount and preferably is present in an amount of from about 100 grams or less to about 500 grams and more preferably from about 200 grams to about 300 grams and even more preferably at about 250 grams. The activated carbon is available from such sources as Calgon. These optional materials are commercially available and various types are also described in the patents and publications incorporated herein by reference. The particle sizes of the above materials are generally in the same ranges as for the SZC and/or ZrP, except for the activated carbon and immobilized enzyme. Preferred ranges are from 20 to about 120 microns for alumina; and from about 0.4 to about 1.2 mm (or 12–50 mesh sieve) for the activated carbon.

Figure 4:
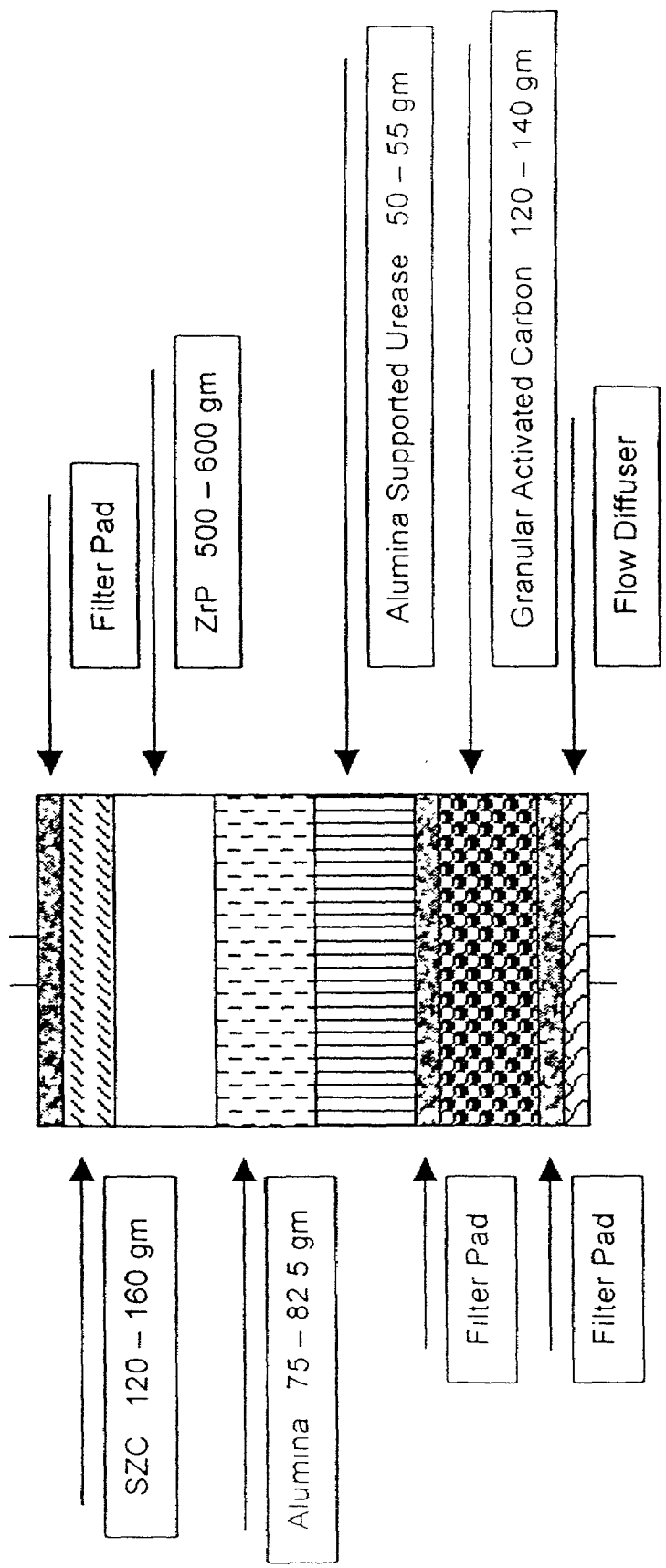
FIGS. 4–6 are exploded views of preferred materials in sorbent cartridges of the present invention.
Figure 5:
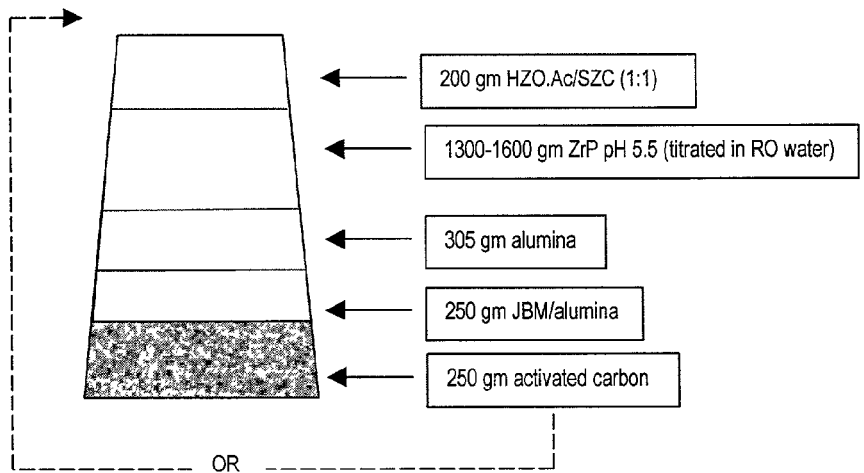
Figure 6:
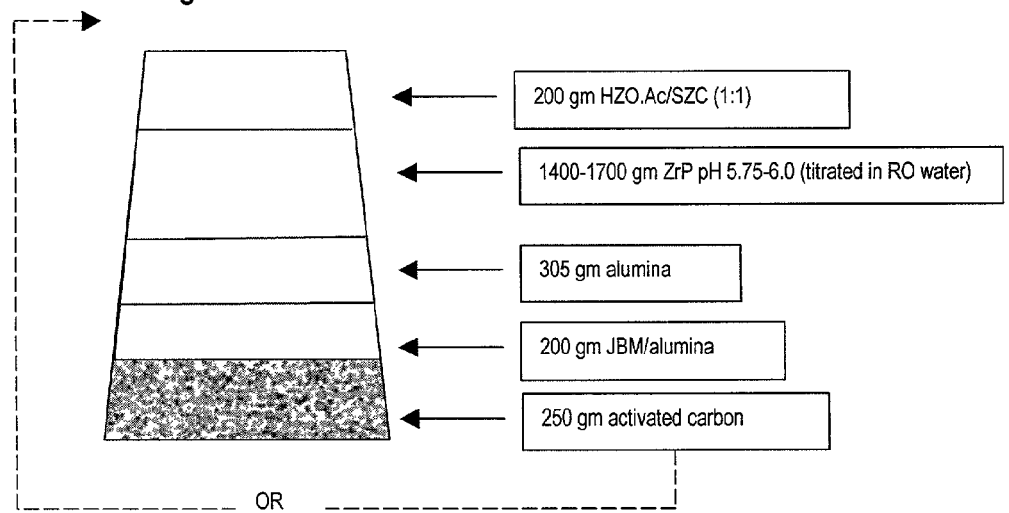

FIGS. 4 through 6 provide exploded views of preferred materials in the adsorbent cartridges of the present invention as well as the preferred arrangement of the various layers contained in the adsorbent cartridges. Preferably, the flow of the spent dialysate fluid enters from the bottom of the cartridge and exits at the top of the cartridge which is more clearly shown in FIG. 8, for instance. FIG. 4 provides a more preferred cartridge set up for the processing of spent dialysate from PD fluids while FIGS. 5 and 6 provide a preferred set up for cartridges useful in the processing of spent dialysate from an HD system. FIG. 5 is a more preferred set up for a cartridge useful for a 4 hour treatment while FIG. 6 is a preferred set up for an 8 hour treatment as described herein. These Figures provide preferred amounts and material layer arrangement. However, as mentioned throughout this application, these various layers can be substituted with other suitable materials or the layers can be rearranged. As indicated in FIGS. 5 and 6, the layer containing the activated carbon or other suitable adsorbent can be located at the bottom of the cartridge and/or at the top of the cartridge.

Figure 8:
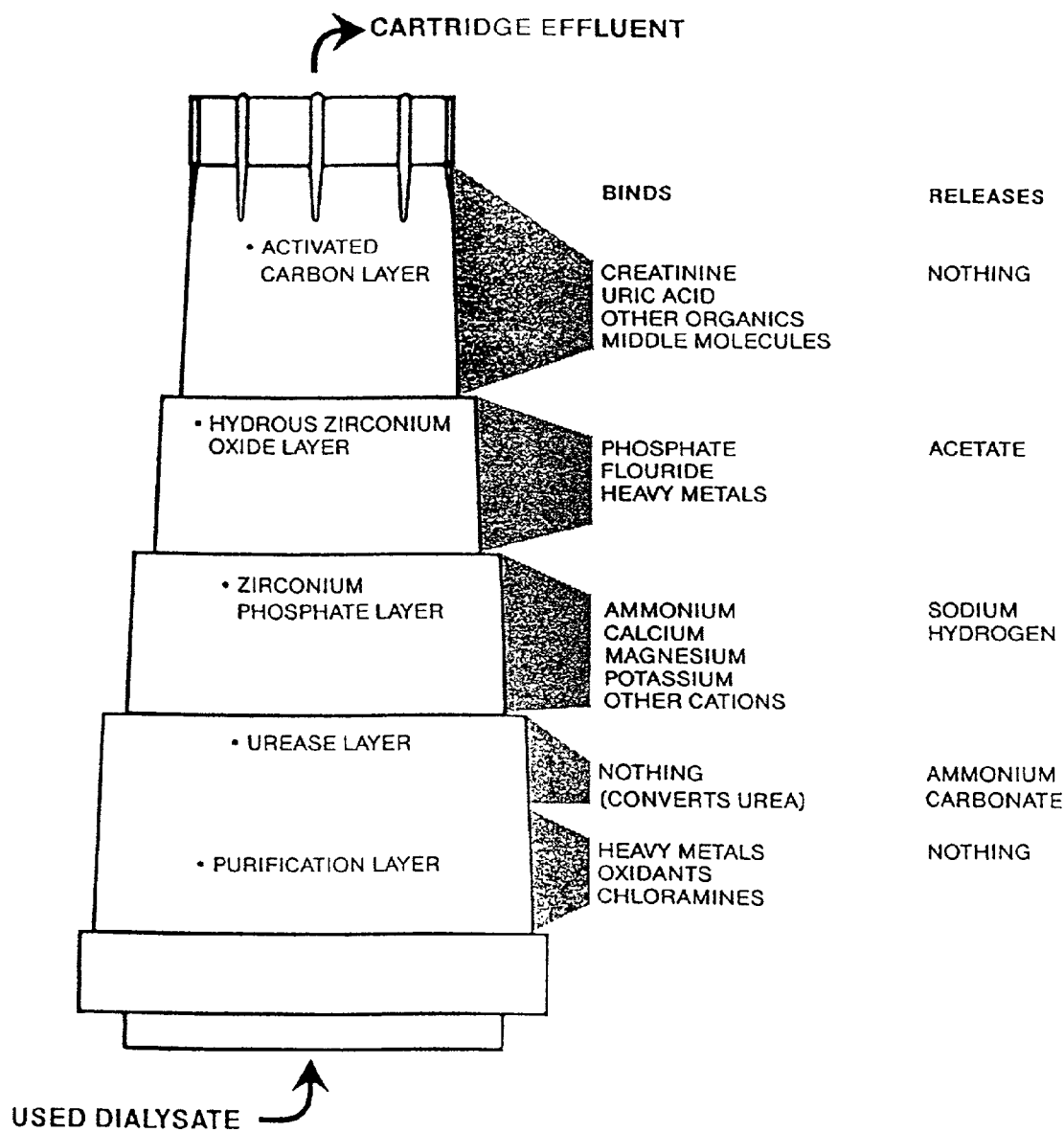
FIG. 8 is a diagram showing a cartridge and the various functions of each layer in a REDY® cartridge.

The various amounts of the various ingredients described throughout this application can be present in effective amounts to accomplish the various functions of each ingredient as set forth, for instance, in FIG. 8. Any combination is possible.

For purposes of the present invention, a sorbent cartridge is any container capable of being used for the separation or purification of a substance (which is preferably a liquid) and more preferably is used dialysate containing waste products and/or excess fluid. The sorbent cartridge generally has an inlet and an outlet and the cartridge can be any shape or size depending upon desired uses. FIG. 1 provides one preferred design of a sorbent cartridge wherein the inlet and the outlet are identified as numeral 11 and numeral 13. Various shapes of the sorbent cartridge include, but are not limited to, a cylindrical shape, rectangular shape, a pyramidal-cylindrical shape as shown, for instance, in FIG. 1 and so on. The shape can be straight-edged or tapered, and so on. Any geometric shape can generally be used.

Preferably, the PD cartridge has the following dimensions: 2 inches–3 inches diameter by 5 inches to 10 inches length. The HD cartridge preferably has the following dimensions: 4 inches–6 inches diameter by 6 inches–12 inches long. Other dimensions can be used depending on the needs of the purifying, amount to purify, operating system and the like. Examples of cartridge designs are further shown in U.S. patent application Ser. No. 6,878,283, entitled "Filter Cartridge Assemblies and Methods of Filtering Fluids" filed Nov. 28, 2001 naming Ralph P. Thompson as the inventor, and this application is incorporated in its entirety by reference herein. Examples of cartridges are also described in one or more of the patents and/or publications identified herein.

Though optional, preferably the above-described materials are arranged in layers preferably in one or more sorbent cartridges. In more detail, preferably, the sodium zirconium carbonate is present as a layer in the sorbent cartridge and the zirconium phosphate is present as a layer in the sorbent cartridge and preferably in the same sorbent cartridge. The layers of the various materials, if used, can be present in any order or combination. More preferably, the alkali metal-Group IV B metal carbonate, preferably sodium zirconium carbonate, is located as the layer closest to the outlet of the sorbent cartridge (i.e., top of cartridge in FIG. 1). In other words, preferably, the used dialysate passes through other layers first, if present, and then passes through the alkali metal-Group IV B metal carbonate or preferably the sodium zirconium carbonate layer. A preferred arrangement of layers is shown in FIG. 4. If an immobilized enzyme layer is present, preferably, this layer is located before the zirconium phosphate layer or other suitable layer, if present. Again, in other words, the used dialysate passes first through the immobilized enzyme layer prior to passing through the layer containing the zirconium phosphate, if present. Furthermore, while the sodium zirconium carbonate can be present any where in the cartridge, preferably the layer containing the sodium zirconium carbonate is located after the layer containing the zirconium phosphate, if present.

A preferred order of layers is as follows, realizing that these layers and the materials in the layers are optional.

a) sodium zirconium carbonate or other alkali metal-Group IV metal-carbonate b) zirconium phosphate or other ammonia adsorbent c) alumina or other like material d) alumina supported urease or other immobilized enzyme layer or other material to convert urea to ammonia such as diatomaceous earth or zirconium oxide e) granular activated carbon or other adsorbent.

Preferably, one or more filter pads can be located throughout the sorbent cartridge to ensure that the layer integrity is maintained during operation. The filter pad can be made of any type of material, for instance, standard filter paper or cellulose pads and the like and typically is the diameter or length-width of the cartridge in order to separate completely one layer from another layer. Preferably, a filter pad is located above and in contact with the sodium zirconium carbonate layer. A second filter pad can be located between and in contact with the alumina supported urease layer and the granular activated carbon layer. A third filter pad can be located between and in contact with the granular activated carbon layer that faces the inlet of the sorbent cartridge. One or more of these filter pads can be used. A flow diffuser which uniformly diffuses the used dialysate throughout the entire width or diameter of the sorbent cartridge can preferably be used. The flow diffuser preferably has a design of radial spreading channels made of plastic or other suitable materials. The flow diffuser is, as shown in FIG. 4, typically located prior to any of the optional filter pads or materials used in the sorbent cartridge and is adjacent to the inlet (or part of the inlet) of the sorbent cartridge. A barrier layer(s) can also be used in the sorbent cartridge. A barrier layer is preferably located between the immobilized enzyme layer and the alumina layer, if present. An example of a barrier layer includes filter paper and the like.

In another embodiment of the present invention, the present invention relates to a particular order of materials present as layers in a sorbent cartridge as follows:

adsorbent layer immobilized enzyme layer or other material to convert urea to ammonia optional barrier layer optional alumina layer ammonia adsorbent phosphate adsorbent optional filter pad As indicated above, preferably the ammonia adsorbent is a zirconium phosphate and the phosphate adsorbent is preferably a sodium zirconium carbonate. This particular arrangement of layers results in an optimal regeneration or purification of the used dialysate. In more detail, the following description of these materials and/or layers or other materials can be used in any combination in the present invention.

1. Immobilized urease or other enzyme layer for enzymatic conversion of urea to ammonium carbonate. The methods to immobilize urease may be categorized as follows:

a. Adsorption, e.g., alumina, activated carbon, anion-exchange resins, diatomaceous earth, or other conventional adsorbents that are commonly employed adsorbents.

b. Covalent bond to water insoluble polymer to form enzyme-polymer conjugates via activation procedure or reactive polymer. The commonly employed water-insoluble supports for the covalent attachment of enzymes may include the following:

| | |
|---|---|
| Synthetic supports, e.g., | Acrylamide-based polymer |
| | Maleic anhydride-based polymers |
| | Polypeptides |
| | Styrene-based polymer |
| Natural Supports, e.g., | Agarose (sepharose) |
| | Dextran (sephadex) |
| | Cellulose |
| | Starch | c. Intermolecular cross-linking of enzyme using multifunctional reagents e.g., glutaraldehyde, hexamethylene diamine. Cross-linking is usually after adsorption on porous support.

d. Entrapment within cross-linked polymers, e.g., polyacrylamide gel.

e. Microencapsulation, e.g. nylon, cellulose nitrate, ethyl cellulose, polyamide.

f. Containment within semi-permeable membrane devices, e.g., Amicon ultra-filtration cells, Dow hollow fiber beaker device.

2. Cation exchange materials in $Na^+$ or $H^+$ form as a $NH_4$-scavenger and adsorbent for infusate cations as well as toxic trace metals in tap water. Another function of the material is to convert carbonate from urea hydrolysis to bicarbonate. These may include cation exchange resins and inorganic ion exchange sorbents (cation type) such as zirconium phosphate, titanium phosphate, zeolite, and the like.

3. Anion exchange materials in $Ac^-$, $HCO_3^-$, $Cl^-$, or $OH^-$ form as a phosphate scavenger and adsorbent for toxic anions in tap water such as $F^-$ and aluminate. Another function of the materials can be to provide base supplement such as acetate and bicarbonate in order to correct for metabolic acidosis of the patient. These may include anion-exchange resins and inorganic ion-exchange sorbent (anion type) such as hydrous zirconium oxide, hydrous silica, stannic oxide, titanium oxide, antimonic acid, hydrous tungsten oxide, sodium zirconium carbonate, and the like.

4. Adsorbent for removal of creatinine, uric acid, and middle molecules of uremic toxins as well as organics in tap water. Although activated carbon is the most effective sorbent for removing nitrogenous waste metabolites, other potential candidates may include certain ion-exchange resins and affinity chromatography materials such as derivatives of cellulose, polystrene gel, polyacrylamide gels, porous glass and agarose and the like.

5. For hemodialysis, a component layer is preferred to remove the chlorine from tap water for dialysis or to use highly purified water. The material can be carbon-impregnated pads, granular activated charcoal, and the like.

In the sorbent cartridge, the component materials can be put in a mixed form or arranged in discrete layers separated by filter papers or cellulose pads, although the efficiency and performance are different. There can be various configurations for the layers. The chlorine removal layer, if used, preferably precedes the urease-immobilized layer since chlorine can deactivate the enzyme. The $NH_{4-}$ scavenger or cation exchange layer preferably succeeds the urease-immobilized layer.

The cartridges of the present invention, as indicated above, can be used in a variety of separation systems and preferably are used in the regeneration or purification of dialysates (e.g., HD) or PD solutions. In the most simplest design, spent or used dialysate or PD solutions can simply be passed through one or more cartridges to purify or regenerate the spent fluids. Such a system can be quite simple in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction, for instance as shown in FIG. 1. In a more elaborate system, the system set forth in FIG. 2 can be used especially for hemodialysis; that is a single pass dialysis system or a system that is preferably used as a closed system as shown in FIG. 3. With respect to the system shown in FIG. 2, in lieu of discarding the used dialysate to a floor drain, as an alternative, the used dialysis can simply be collected in a container which then can be regenerated or purified by passing the spent dialysate through one or more cartridges as described above. More preferably, the sorbent dialysis system shown in FIG. 3 uses a cartridge as described above which is located as indicated in FIG. 3. Such a system permits the continuous reusing of the regenerated dialysate in a patient during dialysis treatment.

With respect to peritoneal dialysis, there are several options. First, like hemodialysis, the peritoneal dialysis solution that is spent can be directly passed through one or more cartridges to purify or regenerate the used peritoneal dialysis solution in order to remove the waste products. Alternatively, the peritoneal dialysis solution which is used or spent can first be passed through a dialyzer in the same manner as blood during hemodialysis wherein dialysate removes waste products and the like from the peritoneal dialysis solution and then the dialysate can be regenerated or purified by passing the used or spent dialysate through the cartridge. Either system can be used in the present invention. With a closed PD system, such as one like FIG. 3, the risk of peritonitis can be reduced significantly since the frequent connections which must be made with conventional systems between the catheter in the peritoneal cavity and a succession of dialysis solution containers is avoided in one embodiment of the present invention.

Figure 2:
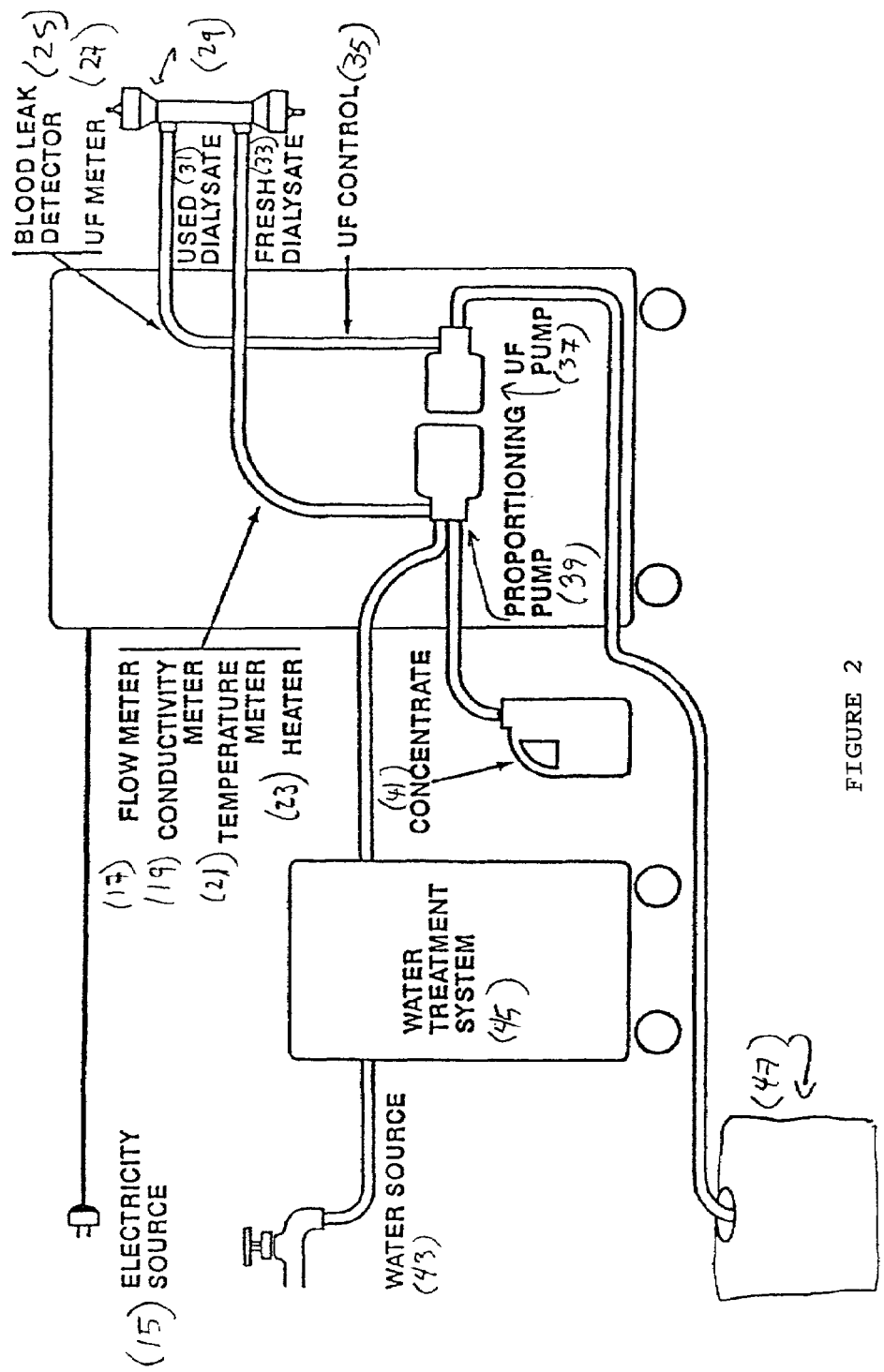
FIG. 2 is a schematic diagram showing a single pass dialysis system.
Figure 3:
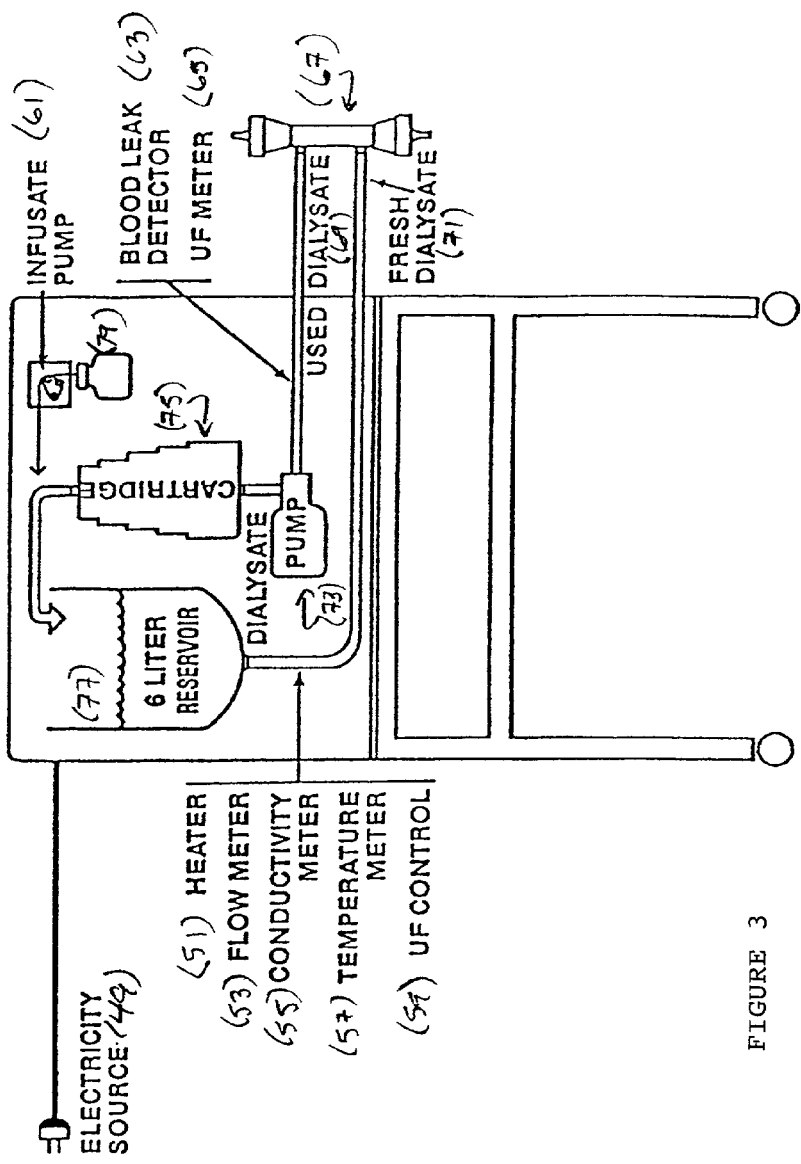
FIG. 3 is a schematic diagram showing a sorbent dialysis system.

In more detail, and referring to FIG. 2, in a single pass dialysis system, 15 identifies a source for electricity to operate the single pass dialysis system. 17 represents a flow meter, 19 represents a conductivity meter, 21 represents a temperature meter, and 23 represents a heater, all of which are conventional items used in single pass dialysis systems and are known to those skilled in the art and can be used in the system of the present invention. 25 represents a blood leak detector and 27 represents a UF meter which again are conventional items in a single pass dialysis system that are understood by those skilled in the art. 29 represents a dialyzer which again is known by those skilled in the art and typically is a system containing a membrane in order to have the waste products pass through the membrane to the dialysate fluid. There are a variety of different dialyzers commercially available and any of these can be used in the present invention. 31 represents the passing of the used dialysis and 33 represents the introduction of fresh dialysate into the dialyzer 29. 35 represents a UF control which is known to those skilled in the art in dialysis systems and conventional units can be used in the present invention. 37 represents a UF pump and 39 represents a proportioning pump which are conventional items in dialysis systems. 41 represents concentrate used to form the fresh dialysate, 43 represents the water used to mix with the concentrate in order to form the fresh dialysate and 45 represents the water treatment system used to purify the water prior to the mixing of the water with the concentrate. Again, these items are conventional in dialysis systems and commercially available items can be used in the present invention. 47 represents a container or drain to collect the used dialysate in order to be purified or regenerated by the cartridges of the present invention.

Referring to FIG. 3, 49 refers to a source of electricity to operate the dialysis system shown in FIG. 3. 51 represents a heater, 53 represents a flow meter, 55 represents a conductivity meter, 57 represents a temperature meter, and 59 represents a UF control. These items are conventional items in a sorbent dialysis system and are known to those skilled in the art and can be used in the present invention as shown in FIG. 3. 61 is an infusate pump that is used to pump in fresh concentrate 79 to be mixed with the regenerated dialysate which ultimately enters the reservoir 77 which is preferably a six liter reservoir. 63 represents a blood leak detector and 65 represents a UF meter which are conventional items in dialysis systems and can be used herein. 67 represents a dialyzer which is the same as in FIG. 2. Similarly, 69 represents used dialysis leaving the dialyzer and 71 represents fresh dialysate entering the dialyzer 67. 73 is a pump to pump the used dialysate from the dialyzer into the cartridge 75 which are the cartridges of the present application.

In a preferred embodiment, the cartridges of the present invention are made for 4 hours of dialysis treatment or for 8 hours of dialysis treatment. Furthermore, the 8 hour cartridges are typically made for home use and the 4 hour cartridges are typically made for dialysis treatment in medical treatment or dialysis centers.

The cartridges of the present invention can generally be used with any type of dialysis system as described above. The flows that pass through the cartridge are typically any conventional flows. For instance, flows from about 50 ml/min or less to 500 ml/min or more of dialysate can flow through the cartridge and can be used in the systems of the present invention. Other flows can be used depending upon the size of the cartridge and the operating system.

The cartridges of the present invention have the ability to maintain and/or restore in dialysate the $Na^+$ and/or $HCO_3^-$ amounts that should be present in fresh dialysate as well as in a patient's blood that is being treated by way of the dialysis system of the present invention. Accordingly, the present invention can restore the $Na^+$ and/or $HCO_3^-$ levels in spent dialysate to proper and acceptable levels, (e.g., for $Na^+$, from about 135 to about 145 mEq/L and for $HCO_3^-$, from about 24 mEq to about 32 mEq/L). As a result, restoring these levels permits the patient's blood to be restored and/or maintained at these levels. This is an impressive capability.

The dialysis systems or components thereof described in the following patents can be used in the present application and these systems can incorporate the materials and/or cartridges of the present invention: U.S. Pat. Nos. 6,309,673; 6,306,836; 6,196,992; 6117,122; 6,074,359; 6,017,942; 5,984,891; 5,955,450; 5,938,634; 5,782,796; 5,631,025; 5,597,805; 4,560,472; 6,299,769; 6,284,131; 6,146,536; 5,968,966; 5,704,915; 5,824,213; 5,641,405; 4,738,668; 6,293,921; 6,284,139; 6,274,103; 5,980,481; and 5,498,338. All of these patents are incorporated in their entirety by reference herein and form a part of the present application.

There are numerous uses for the materials of the present invention and especially the cartridges of the present invention such as the regeneration of dialysis fluids as mentioned above. Furthermore, the cartridges can also be used in any separation process which requires the removal of impurities or waste products from a fluid or other medium that is passable through the materials of the present invention. Also, the present invention is quite useful with respect to treating drug overdose patients or other patients which are in need or removing undesirable or dangerous contaminants in a person's system. Accordingly, the present invention provides useful embodiments that allow the regeneration of dialysate type fluids and other fluids.

The present invention will be further clarified by the following examples, which are intended to be purely exemplary of the present invention.

EXAMPLES

Figure 7:
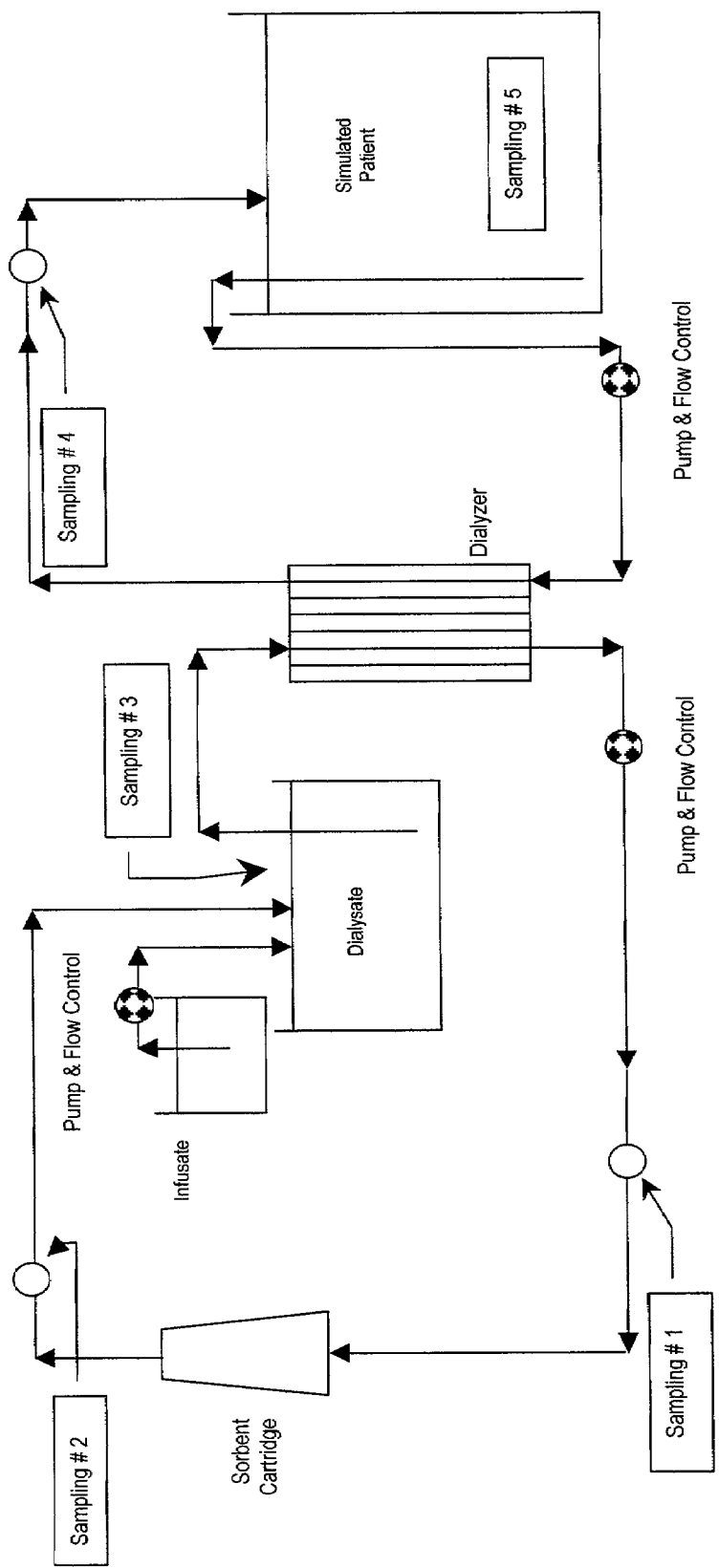
FIG. 7 is a schematic diagram showing a dialysis test set-up to test the cartridges of the present invention.

The dialysate regeneration system was set up as shown in FIG. 7. As shown in FIG. 7, a test system can be arranged wherein there are various locations where the sampling of the dialysate fluid can occur as well as sampling of the simulated patient fluid which can be the simulation of the waste products found in blood or a PD fluid. In more detail, Sampling No. 1 provides the ability to sample the content of the spent dialysate fluid or PD fluid prior to its entry into the cartridge. Sampling No. 2 permits the testing of the dialysate or PD fluid once it has been regenerated by the cartridge of the present invention. Sampling No. 3 permits the sampling of the regenerated dialysate fluid or PD fluid after the fluid has been infused with the standard components of an infusate which typically introduces calcium and magnesium ions so as to restore them to acceptable levels. Other components can also be restored by the infusate. Sampling No. 4 permits the testing of the contents of the simulated fluids of a patient after passing through the dialyzer containing general waste products typically found in blood or PD fluid or the like. The remaining components as shown in FIG. 7 are conventional with respect to the mechanical set up and the use of sample ports, flow meters, flow controls, pumps, power controls, dialyzers, and the like.

Example 1

Cartridge for HD Regeneration

In this model, the patient was represented by a simulated fluid bath of 60 liters volume of the following composition at 37° C.

| | |
|---|---|
| $NaHCO_3$ | 25 mEq/L |
| NaCl | 115 mEq/l |
| $CaAc_2.H_2O$ | 3 mEq/L |
| $MgAc_2.4H_2O$ | 1 mEq/L |
| KAc (anhydrous) | 2 mEq/L |
| Dextrose | 100 mg % |
| pH | 7–7.4 |
| Uremic Toxins Levels: | |
| BUN | ~85 mg % |
| Creatinine | ~9 mg % |
| $PO_4$—P | ~6 mg % |

The simulated patient was dialyzed by using a Baxter PSN-120 dialyzer at the blood flow rate (BFR) of 180 ml/min. The 6L dialysate was made up in tap water with a starting concentration as follows:

| | |
|---|---|
| $NaHCO_3$ | 140 mEq/L |
| NaCl | 0 mEq/l |
| Dextrose | 100 mg % |
| pH | 8.1 |

In one experiment, the spent dialysate was regenerated by a sorbent cartridge of the following configuration at the dialysate flow rate (DFR) of 250 ml/min.

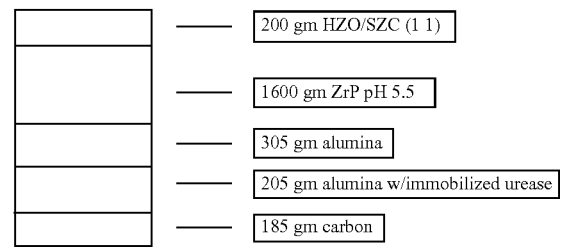

200 gm HZO/SZC (1 1)

1600 gm ZrP pH 5.5

305 gm alumina 205 gm alumina w/immobilized urease 185 gm carbon

Infusate was provided at a calibrated flow rate to maintain $Ca^{2+}$, $Mg^{2+}$, and $K^+$ balance in the regenerated dialysate. The efficacy and performance of the treatment are demonstrated by the following results:

Uremic Toxin Level

Efficacy

| | |
|---|---|
| Pre-dialysis BUN level | 85 mg % |
| Pre-dialysis creatinine level | 9.5 mg % |
| Pre-dialysis $PO_4$—P level | 4.7 mg % |
| Post-dialysis BUN level | 36.6 mg % |
| Post-dialysis creatinine level | 5.2 mg % |
| Post-dialysis $PO_4$—P level | 2.8 mg % |

Amount of Uremic Toxin Removal from Patient and Adsorption Capacity of Cartridge

| | |
|---|---|
| BUN | 29 gm |
| Creatinine | 2.6 gm |
| $PO_4$—P | 1.16 gm |

These amounts of uremic toxin removal should meet the dialysis requirement based on kT/v.

Performance

| | |
|---|---|
| Pressure generated by cartridge: | 24 psi max. |

Composition of cartridge effluent during treatment:

| | |
|---|---|
| $NH_4$—N | 0 mg % |
| BUN | 0.2 mg % |
| $Ca^{2+}$ | 0 mEq/L |
| $Mg^{2+}$ | 0.2 mEq/L |
| $K^+$ | <0.3 mEq/L |
| $PO_4$—P | 0 mg % |
| Creatinine | <0.8 mg % |

$Na^+$ and Bicarbonate Balance in Dialysate and Patient Fluid

The $Na^+$ level in cartridge outlet variation range was 132–155 mEq/L during treatment.

| | |
|---|---|
| Pre-dialysis $Na^+$ of patient | 136 mEq/l |
| Post-dialysis $Na^+$ of patient | 138 mEq/L |
| Pre-dialysis bicarbonate of patient | 24 mEq/L |
| Post-dialysis bicarbonate of patient | 25 mEq/L |

The above-described HD experiment was repeated using a variety of different parameters. The parameters that were varied are set forth in the Tables below. In each case, the cartridge having the various identified materials operated within acceptable parameters with respect to regenerating the dialysate.

| Test # | Dialysis Conditions $DFR/BFR$ | Dialyzer | $HZO/SZC$ $k_{(ml/min)}$ | ZP Amt gm | ZP gm | ZP pH | $NaHCO_3$ Dialysate mEq/L | Pre-Dialysis BUN $mg/DL$ | Patient Fluid Volume liters |
|---|---|---|---|---|---|---|---|---|---|
| 3 | 400/400 | Fresenius 7NR | 256 | 75/125 | 1300 | 5.5 | 40 | 87.5 | 40 |
| 4 | 400/400 | Fresenius 7NR | 256 | 100/100 | 1600 | 5.5 | 60 | 104.7 | 55 |
| 5 | 250/180 | PSN-120 | 125 | 140/60 | 1400 | 6 | 140 | 71.9 | 40 |
| 6 | 250/180 | PSN-120 | 125 | 100/100 | 1600 | 5.75 | 140 | 46 | 42 |
| 7 | 250/180 | PSN-120 | 200 | 100/100 | 1600 | 5.75 | 140 | 85 | 61 |

Results

| Test # | Treatment Time min | Urea-N Hydrolyzed gm | $Na^+$ Post- mEq/L | $Na^+$ Pre- mEq/L | Bicarbonate Post- mEq/L | Bicarbonate Pre- mEq/L |
|---|---|---|---|---|---|---|
| 3 | 173 | 23.4 | 144 | 137 | 26 | 25 |
| 4 | 235 | 38 | 142 | 139 | 26 | 21 |
| 5 | 420 | 20.71 | 142 | 135 | 31 | 24 |
| 6 | >480 | 14.7 | 141 | 138 | 20 | 25 |
| 7 | 420 | 29.5 | 138 | 136 | 26 | 24 |

Ave. $Na^+$ Donation per mEq Cation or $NH_4^+$ Adsorbed: ZrP pH 5.5, 0.106 mEq $Na^+$
ZrP pH 6.25, 0.2266 mEq $Na^+$

| | | | Total Infusate Cations & $NH^{4+}$ Ions Adsorbed by ZrP | | |
|---|---|---|---|---|---|
| Test # | ZrP Amt (grams) | ZrP pH | $Ca^{2+}$, $Mg^{2+}$, $K^+$ (mEq) | $NH_4^+$ (mEq) | Total (mEq) |
| 3 | 1300 | 5.5 | 415 | 1671 | 2086 |
| 4 | 1600 | 5.5 | 564 | 2714 | 3278 |
| 5 | 1400 | 6 | 630 | 1479 | 2109 |
| 6 | 1600 | 5.75 | 720 | 1050 | 1770 |
| 7 | 1600 | 5.75 | 630 | 2109 | 2739 |

| | Patient Na+ Balance | | | Na+ Donation per mEq Cation/NH4 + |
|---|---|---|---|---|
| Test # | Post- mEq/L | Pre- mEq/L | Gain mEq/L | Adsorbed mEq Na+ |
| 3 | 144 | 137 | +280 | 0.1342 |
| 4 | 142 | 139 | +165 | 0.0503 |
| 5 | 142 | 135 | 280 | 0.1328 |
| 6 | 141 | 138 | 126 | 0.0712 |
| 7 | 138 | 136 | 122 | 0.0445 |

GAIN = (Post-dialysis Na+ Level − Pre-dialysis Na+ Level) × patient dialyzable fluid volume V

Example 2

Cartridge for PD Fluid Regeneration

The two-loop PD regenerative system using a dialyzer was set up according to FIG. 7. The spent PD fluid was represented by a simulation bath of the following composition:

| Dextrose | 100 mg % |
|---|---|
| Na+ | 138 mEq/L |
| Ca$^{2+}$ | 2.5 mEq/L |
| Mg$^{2+}$ | 1.0 mEq/L |
| Cl− | 113 mEq/L |
| HCO$_3$− | 25 mEq/L |
| BUN | 20 mg % |
| Creatinine | 3.6 mg % |
| PO$_4$—P | 4.1 mg % |
| pH | 7.4 |

The spent PD fluid was contained in a 15 L PD bag and dialyzed by a Baxter CA50 dialyzer while it is re-circulated by pump at the flow rate of 100 ml/min. Uremic toxins (urea, creatinine, and phosphate) were continuously added to the regenerated PD fluid to simulate peritoneal dialysis in action and to replace the amount removed by the regenerative dialysis. The dialysate used for the regenerative dialysis was a bicarbonate solution of the following composition contained in a 4 L PD bag.

| Dextrose | 1.5% |
|---|---|
| Na+ | 135 mEq/L |
| Ca$^{2+}$ | 2.9 mEq/L |
| Mg$^{2+}$ | 0.5 mEq/L |
| Cl− | 92 mEq/L |
| HCO$_3$− | 31 mEq/L |
| pH | 7.4 |

The dialysate was re-circulated through a sorbent cartridge for purification at the flow rate of 100 ml/min, and provided continuously with infusate after regeneration to replace the Ca$^{2+}$ and Mg$^{2+}$ removed by the cartridge, so that the Ca$^{2+}$ and Mg$^{2+}$ levels in the PD fluid can be maintained and controlled.

The sorbent cartridge used to purify the PD dialysate has the following configuration:

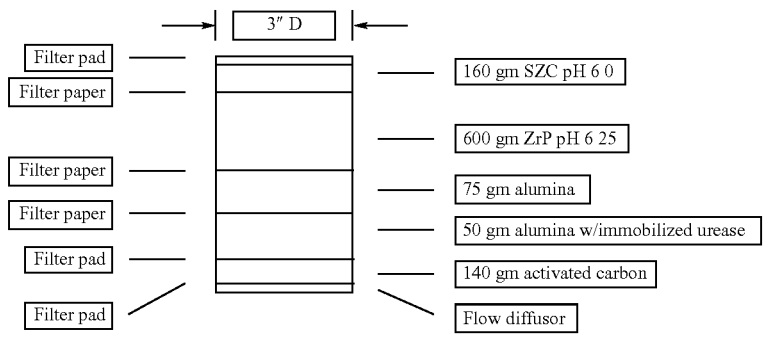

The cartridge served to continuously remove the uremic toxins (urea, creatinine, and phosphate) that were dialyzed across the dialyzer from the spent PD fluid into the dialysate. At the same time, it served to remove the Ca$^{2+}$ and Mg$^{2+}$ from the dialysate so that with the help of infusate provisions, the balance of these ions in the PD fluid was maintained.

The efficacy and performance of the cartridge can be summarized as follows:

Efficacy

The uremic toxin removal for an 8-hour treatment at 100 ml/min dialysate flow rate were as shown below:

| BUN | 4.8 gm |
|---|---|
| Creatinine | 0.96 gm |
| PO$_4$—P | 0.48 gm |

Performance

Electrolyte balance of PD fluid and dialysate before and after dialysis:

|  | PD Fluid | | Dialysate | |
| --- | --- | --- | --- | --- |
|  | Pre-Dialysis | Post-Dialysis | Pre-Dialysis | Post-Dialysis |
| $Na^+$ mEq/L | 141 | 137 | 135 | 145 |
| $HCO_3^-$ mEq/L | 26.5 | 25 | 31 | 33.5 |
| $Ca^{2+}$ mEq/L | 3.0 | 3.0 | 2.9 | 2.8 |
| $Mg^{2+}$ mEq/L | 1.0 | 1.0 | 1.0 | 1.0 |

Adsorption efficiency: No leakage of uremic toxic and $Ca^{2+}$, $Mg^{2+}$, were observed from the cartridge.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed is:

1. A sorbent cartridge comprising at least two layers, wherein one of said layers comprises at least sodium zirconium carbonate in said sorbent cartridge.

2. The sorbent cartridge of claim 1, wherein wherein one of said layers consists essentially of sodium zirconium carbonate.

3. The sorbent cartridge of claim 1, further comprising zirconium phosphate.

4. The sorbent cartridge of claim 3, wherein said zirconium phosphate is present as a layer in said sorbent cartridge.

5. The sorbent cartridge of claim 3, wherein said zirconium phosphate comprises a H+ content of from about 1.4 to about 2.0 wt %;
   a Na+ content of from about 4 to about 6 wt%;
   a $ZrO_2$ wt % of from about 34 wt % to about 37 wt %;
   a $PO_4$ wt % of from about 41 wt % to about 43 wt %; and
   a $H_2O$ wt % of from about 14 wt % to about 18 wt %, based on the weight of the zirconium phosphate.

6. The sorbent cartridge of claim 3, wherein said zirconium phosphate has at least one of the following characteristics:
   a) an adsorption capacity for ammonia of from about 20 mg $NH_4$-N/gm ZrP to about 45 mg $NH_4$-N/gm ZrP;
      an adsorption capacity for $Ca^{2+}$ of from about 2 mEq $Ca^{2+}$/gm ZrP to about 7 mEq $Ca^{2+}$/gm ZrP;
      an adsorption capacity for $Mg^{2+}$ of from about 1 mEq $Mg^{2+}$/gm ZrP to about 5 mEq $Mg^{2+}$/gm ZrP; and
      an adsorption capacity for toxic heavy metals of from about 3 mEq HM/gm ZrP to about 9 mEq HM/gm ZrP;
   b) a $Na^+$ content of from about 1.8 mEq $Na^+$/gm ZrP to about 3 mEq $Na^+$/gm ZrP at a pH of from about 5.5 to about 6;
   c) a minimum leachable $PO_4^{3-}$ of less than about 0.05 mg $PO_4^{3-}$/gm ZrP; or
   d) satisfying ANSI/AAMI RD-5-1992 standard on extractable toxic impurities.

7. The sorbent cartridge of claim 5, wherein said zirconium phosphate has no residual sulfate or chloride.

8. The sorbent cartridge of claim 5, wherein said zirconium phosphate has less than 0.01% sulfate, chloride, or both.

9. The sorbent cartridge of claim 3, wherein said zirconium phosphate in $H_2O$ has a pH of from about 6 to about 7.

10. The sorbent cartridge of claim 3, wherein said zirconium phosphate has an average grain size of from about 30 to about 40 microns.

11. A sorbent cartridge comprising an alkali metal-Group IV B metal carbonate, wherein said alkali metal-Group IV B metal carbonate is present as a layer in said sorbent cartridge.

12. The sorbent cartridge of claim 11, further comprising a Group IV B metal phosphate.

13. The sorbent cartridge of claim 1, further comprising alumina, alumina supported urease, granular activated carbon, or combinations thereof.

14. The sorbent cartridge of claim 13, wherein said alumina, alumina supported urease, and granular activated carbon are each present as separate layers in said sorbent cartridge.

15. The sorbent cartridge of claim 14, wherein said layers have the following order:
   a) said sodium zirconium carbonate;
   b) a zirconium phosphate;
   c) said alumina;
   d) said alumina supported urease;
   e) said granular activated carbon.

16. The sorbent cartridge of claim 15, wherein said sorbent cartridge further comprises a first filter pad located above and in contact with said sodium zirconium carbonate, a second filter pad is located between and in contact with said alumina supported urease and said granular activated carbon, and a third filter pad is located beneath and in contact with said granular activated carbon.

17. The sorbent cartridge of claim 16, further comprising a flow diffuser located beneath and in contact with said third filter pad.

18. The sorbent cartridge of claim 1, wherein said sodium zirconium carbonate comprises from about 2 wt % to about 5 wt % $Na^+$;
   from about 44 wt % to about 50 wt % $ZrO_2$;
   from about 12 wt % to about 18 wt % $CO_3^{2-}$; and
   from about 30 wt % to about 40 wt % LOD, based on the weight of the sodium zirconium carbonate.

19. The sodium zirconium carbonate of claim 1, wherein said sodium zirconium carbonate satisfies ANSI/AAMI RD-5-1992 standard on extractable toxic impurities.

20. The sodium zirconium carbonate of claim 1, wherein said sodium zirconium carbonate satisfies at least one of the following characteristics:
   a phosphate adsorption having a minimum capacity of from about 30 to about 35 $mgPO_4$-P/gm SZC;
   a minimum $HCO_3^-$ content of from about 2 to about 4 mEq $HCO_3^-$ per gm SZC;
   a leachable $Na^+$ content of from about 1.5 to about 2.0 mEq $Na^+$/gm SZC;
   or a pH range of titrated sodium zirconium carbonate of from about 6 to about 7.

21. The sorbent cartridge of claim 1, further comprising hydrous zirconium oxide.

22. The sorbent cartridge of claim 21, wherein said hydrous zirconium oxide is in the acetate form.

23. The sorbent cartridge of claim 22, wherein said sodium zirconium carbonate and said hydrous zirconium oxide are present in a weight ratio of about 1 to 1.

24. The sorbent cartridge of claim 22, wherein said sodium zirconium carbonate and said hydrous zirconium oxide are present in a same layer and are blended together.

25. The sorbent cartridge of claim 1, further comprising zirconium basic carbonate.

26. The sorbent cartridge of claim 25, wherein said zirconium basic carbonate comprises $Na^+$ of less than about 1000 ppm;
a $ZrO_2$ wt % of from about 35 wt % to about 40 wt%;
and a $CO_3^{2-}$ of from about 8 wt % to about 10 wt %, based on the weight of the zirconium basic carbonate.

27. The sorbent cartridge of claim 26, wherein said zirconium basic carbonate has about 0 wt % $SO_4^{2-}$ and about 0 wt % $Cl^-$.

28. The sorbent cartridge of claim 1, wherein said sodium zirconium carbonate is present in said cartridge in an amount of from about 100 grams to about 300 grams.

29. The sorbent cartridge of claim 28, wherein said cartridge further comprises zirconium phosphate in an amount of from about 300 grams to about 1900 grams.

30. The sorbent cartridge of claim 29, further comprising alumina in the amount of from about 100 grams to about 500 grams, immobilized enzyme in an amount of from about 100 grams to about 300 grams, and activated carbon or other adsorbent in an amount of from about 100 grains to about 500 grams.

31. The sorbent cartridge of claim 1, further comprising an immobilized enzyme material capable of enzymatic conversion of urea to ammonium carbonate, a cation exchange material in the sodium or hydrogen form, an anion exchange material in the $Ac^-$, $HCO_3^-$, $Cl^-$, or $OH^-$ form, and an adsorbent capable of removing creatinine, uric acid, or both.

32. The sorbent cartridge of claim 31, further comprising a chlorine removal material.

33. The sorbent cartridge of claim 32, wherein the materials are present as two or more layers in said cartridge.

34. The sorbent cartridge of claim 32, wherein the materials are present as two or more layers in said cartridge.

35. The sorbent cartridge of claim 11, further comprising an immobilized enzyme material capable of enzymatic conversion of urea to ammoniuin carbonate, a cation exchange material in the sodium or hydrogen form, an anion exchange material in the $Ac^-$, $HCO_3^-$, $Cl^-$, or $OH^-$ form, and an adsorbent capable of removing creatinine, uric acid, or both.

36. The sorbent cartridge of claim 11, further comprising a chlorine removal material.

37. The sorbent cartridge of claim 11, wherein the materials are present as two or more layers in said cartridge.

38. A method to regenerate or purify spent dialysis fluid comprising passing said spent dialysis fluid through the sorbent cartridge of claim 1.

39. A method to regenerate or purify spent dialysis fluid comprising passing said spent dialysis fluid through the sorbent cartridge of claim 3.

40. A method to regenerate or purify spent dialysis fluid comprising passing said spent dialysis fluid through the sorbent cartridge of claim 4.

41. A method to regenerate or purify spent dialysis fluid comprising passing said spent dialysis fluid trough the sorbent cartridge of claim 5.

42. A method to regenerate or purify spent dialysis fluid comprising passing said spent dialysis fluid through the sorbent cartridge of claim 6.

43. A method to regenerate or purify spent dialysis fluid comprising passing said spent dialysis fluid through the sorbent cartridge of claim 11.

44. (withdrawn): A method to regenerate or purify spent dialysis fluid comprising passing said spent dialysis fluid through the sorbent cartridge of claim 12.

45. A method to regenerate or purify spent dialysis fluid comprising passing said spent dialysis fluid through the sorbent cartridge of claim 15.

46. An apparatus for conducting dialysis comprising the sorbent cartridge of claim 1, a dialyzer in fluid communication with said cartridge wherein spent dialysis fluid passes from said dialyzer to and through said cartridge.

47. The apparatus of claim 46, wherein said spent dialysis fluid is spent hemodialysis fluid.

48. The apparatus of claim 46, wherein spent dialysis fluid is restored to original balance of $Na^+$ and $HCO_3^-$ contents found in fresh dialysate.

49. The apparatus of claim 46, wherein said dialyzer is in fluid communication with the blood of a patient.

50. The apparatus of claim 49, wherein the $Na^+$ and $HCO_3^-$ balance in said blood is restored to levels found in healthy patient without renal problems.

51. The apparatus of claim 46, wherein said spent dialysis fluid is spent dialysate fluid obtained from a dialyzer wherein spent peritoneal dialysis fluid is passed through said dialyzer and cleaned by fresh dialysate fluid.

52. A dialysis system comprising the sorbent cartridge of claim 1 and a source of spent peritoneal dialysis solution, wherein the source of said spent peritoneal dialysis solution is in fluid communication with said cartridge wherein said spent peritoneal dialysis solution passes to and through said cartridge.

53. The sorbent cartridge of claim 1, wherein said cartridge is capable of restoring the balance of $Na^+$ and $HCO_3^-$ in spent dialysate to levels found in fresh dialysate.

54. The sorbent cartridge of claim 5, wherein said cartridge is capable of restoring the balance of $Na^+$ and $HCO_3^-$ in spent dialysate to levels found in fresh dialysate.

55. The sorbent cartridge of claim 30, wherein said cartridge is capable of restoring the balance of $Na^+$ and $HCO_3^-$ in spent dialysate to levels found in fresh dialysate.

56. The sorbent cartridge of claim 3, wherein said zirconium phosphate is further away from an inlet opening of said sorbent cartridge than said layer of sodium zirconium carbonate.

57. The sorbent cartridge of claim 4, wherein said layer of zirconium phosphate is further away from an inlet opening of said sorbent cartridge than said layer of sodium zirconium carbonate.

* * * * *

UNITED STATES PATENT AND TRADEMARK OFFICE
CERTIFICATE OF CORRECTION

| | | |
|---|---|---|
| PATENT NO. | : 7,033,498 B2 | Page 1 of 1 |
| APPLICATION NO. | : 09/996505 | |
| DATED | : April 25, 2006 | |
| INVENTOR(S) | : Wong | |

It is certified that error appears in the above-identified patent and that said Letters Patent is hereby corrected as shown below:

IN THE CLAIMS:

Claim 33, column 23, line 35, "claim 32" should read --claim 31--

Claim 35, column 23, line 41, "ammoniuin" should read --ammonium--

Claim 41, column 23, line 59, "trough" should read --through--

Claim 44, column 24, line 8, "(withdrawn)" should be deleted.

Signed and Sealed this

Fourth Day of July, 2006

JON W. DUDAS
*Director of the United States Patent and Trademark Office*